US011684523B2

(12) United States Patent
Toro et al.

(10) Patent No.: US 11,684,523 B2
(45) Date of Patent: *Jun. 27, 2023

(54) ABSORBENT ARTICLES WITH THINNER BACKSHEET

(71) Applicant: The Procter & Gamble Company, Cincinnati, OH (US)

(72) Inventors: Carlo Toro, Crailsheim (DE); Stefan Roell, Bensheim (DE); Jay Tao, Mason, OH (US); David Mark Ooten, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 151 days.

This patent is subject to a terminal disclaimer.

(21) Appl. No.: 17/341,672

(22) Filed: Jun. 8, 2021

(65) Prior Publication Data
US 2021/0290451 A1 Sep. 23, 2021

Related U.S. Application Data

(63) Continuation of application No. 14/972,271, filed on Dec. 17, 2015, now Pat. No. 11,058,590, which is a (Continued)

(30) Foreign Application Priority Data

Dec. 15, 2014 (EP) .................................. 14197944

(51) Int. Cl.
*A61F 13/514* (2006.01)
*A61F 13/472* (2006.01)
(Continued)

(52) U.S. Cl.
CPC ...... *A61F 13/51401* (2013.01); *A61F 13/472* (2013.01); *A61F 13/5605* (2013.01);
(Continued)

(58) Field of Classification Search
CPC .................. A61F 13/472; A61F 13/514; A61F 13/51401; A61F 13/5605; A61F 13/5616;
(Continued)

(56) References Cited

U.S. PATENT DOCUMENTS 4,337,772 A 7/1982 Roeder
4,690,680 A 9/1987 Higgins
(Continued)

FOREIGN PATENT DOCUMENTS

EP 0471384 B1 10/1996
EP 0745368 A1 12/1996
(Continued)

OTHER PUBLICATIONS

CM04169FQ Third Party Opposition for 14197944.3 dated May 18, 2020, 12 pages.
(Continued)

*Primary Examiner* — Michele Kidwell
(74) *Attorney, Agent, or Firm* — Amanda Herman Berghauer; Gary J. Foose (57) ABSTRACT

An absorbent article selected from a sanitary napkin, an incontinence pad and a pantyliner, comprising a topsheet layer a backsheet layer a fastening adhesive applied on the backsheet garment facing surface, wherein at least a portion of said fastening adhesive (PFA) is applied in a pattern and wherein said backsheet layer is a plastic film having a basis weight of less than 20 gsm.

18 Claims, 2 Drawing Sheets

Related U.S. Application Data continuation of application No. PCT/US2015/064729, filed on Dec. 9, 2015.

(51) Int. Cl.
*A61F 13/56* (2006.01)
*A61F 13/47* (2006.01)

(52) U.S. Cl.
CPC .. *A61F 13/5616* (2013.01); *A61F 2013/4708* (2013.01); *A61F 2013/51409* (2013.01)

(58) Field of Classification Search
CPC .... A61F 2013/4708; A61F 2013/51409; A61F 2013/51417
See application file for complete search history.

(56) References Cited

U.S. PATENT DOCUMENTS

| | | | |
|---|---|---|---|
| 5,217,448 | A | 6/1993 | Glaug et al. |
| 5,578,026 | A | 11/1996 | Lavash et al. |
| 5,591,153 | A | 1/1997 | Mattingly, III |
| 5,690,624 | A | 11/1997 | Sasaki et al. |
| 6,096,420 | A | 8/2000 | Wilhoit et al. |
| 6,258,076 | B1 | 7/2001 | Glaug et al. |
| 6,420,625 | B1 | 7/2002 | Jones |
| 6,443,836 | B1 | 9/2002 | Horejsi et al. |
| 11,058,590 | B2 | 7/2021 | Toro et al. |
| 2002/0013559 | A1* | 1/2002 | Shimizu .................. A61L 15/28 604/385.03 |
| 2002/0029027 | A1 | 3/2002 | Rangel et al. |
| 2003/0065299 | A1 | 4/2003 | Carlucci |
| 2003/0163109 | A1 | 8/2003 | Ohba et al. |
| 2005/0043699 | A1 | 2/2005 | Minato |
| 2006/0084340 | A1 | 4/2006 | Bond et al. |
| 2009/0062761 | A1 | 3/2009 | Goerg-wood et al. |
| 2009/0157033 | A1 | 6/2009 | Toro et al. |
| 2010/0191210 | A1 | 7/2010 | Hayashi et al. |
| 2011/0028927 | A1 | 2/2011 | Bellucci et al. |
| 2011/0144604 | A1 | 6/2011 | Noda et al. |
| 2011/0152812 | A1 | 6/2011 | Hird |
| 2011/0213324 | A1 | 9/2011 | Chen et al. |
| 2012/0041410 | A1 | 2/2012 | Ueda |
| 2014/0186566 | A1 | 7/2014 | Wood |
| 2014/0248484 | A1 | 9/2014 | Bormann et al. |
| 2014/0257220 | A1 | 9/2014 | Neton et al. |
| 2016/0143791 | A1* | 5/2016 | Wood .................. A61F 13/025 24/304 |
| 2016/0331604 | A1 | 11/2016 | Hao et al. |
| 2017/0135864 | A1 | 5/2017 | Nomoto |
| 2020/0107974 | A1 | 4/2020 | Persson et al. |
| 2020/0281782 | A1 | 9/2020 | Roell et al. |

FOREIGN PATENT DOCUMENTS

| | | |
|---|---|---|
| EP | 0923921 A1 | 6/1999 |
| EP | 2081102 A1 | 7/2009 |
| GB | 2081102 A | 2/1982 |
| JP | H04259459 A | 9/1992 |
| JP | 2003010245 A | 1/2003 |
| JP | 2006247088 A | 9/2006 |
| JP | 2006296974 A | 11/2006 |
| JP | 2007130274 A | 5/2007 |
| JP | 2007135660 A | 6/2007 |
| JP | 2007135661 A | 6/2007 |
| JP | 2007236552 A | 9/2007 |
| JP | 2012050716 A | 3/2012 |
| WO | 0139708 A2 | 6/2001 |
| WO | 2009072367 A1 | 6/2009 |

OTHER PUBLICATIONS

CM04169FQ Third Party Opposition for 14197944.3 dated May 25, 2020, 27 pages.
All Office Actions, U.S. Appl. No. 14/972,271.
ASDA PI Classic Value Multi 10×30p, SCA Hygiene Products, Dec. 3, 2009, 16 Pages.
European Search Report and Search Opinion; Application Ser. No. 14197944.3 dated Jun. 8, 2015; 5 pages.
International Search Report and Written Opinion; Application Ser. No. PCT/US/S2015/064729 dated Mar. 11, 2016; 9 pages.
All Office Actions for U.S. Appl. No. 14/972,271, filed Dec. 17, 2015.

* cited by examiner

ABSORBENT ARTICLES WITH THINNER BACKSHEET

FIELD OF THE INVENTION

The present invention relates to absorbent articles comprising a thin plastic film as backsheet and a patterned application of fastening adhesive on the garment facing side of the backsheet.

BACKGROUND OF THE INVENTION

Absorbent articles for personal hygiene which during use are attached to the underwear of the user are known in the art. Typical examples include sanitary napkins, pantyliners and incontinence pads. Such articles are commonly used to absorb and retain bodily fluids and other exudates excreted by the human body, such as urine and menses. These absorbent articles typically comprise a topsheet, a backsheet, and, optionally, an absorbent core disposed between the topsheet and backsheet and a fastening adhesive applied on the garment facing surface of the backsheet and are disposable after single use.

There is a continuous interest from the industry in reducing the environmental impact of disposed absorbent articles and one approach in this direction is to reduce the use of plastic materials in absorbent articles. In particular, in the case of absorbent articles using a plastic film as the backsheet, there is a desire to use lighter and thinner plastic films so to reduce the consumption of plastic and improve the tactile perception by the user as thinner films are softer.

A problem connected to the use of thinner films as backsheets is that absorbent articles require to include a strong fastening adhesive applied onto the garment facing surface of the backsheet so that, when the article is applied onto the user's undergarment before usage, it adheres strongly to the undergarment and maintains its position when the user exerts pressure on it from all directions while conducting normal daily activities such as for example walking, sitting and so on.

When removing the absorbent article from the underwear the article is typically peeled off from the undergarment from one side to the other detaching the backsheet from the undergarment and, if the backsheet is too weak, in the presence of strong adhesion of the fastening adhesive, it is possible that a tear of the backsheet occurs.

This is highly undesirable because a torn backsheet exposes the content of the absorbent core thus creating a hygienic problem, and additionally fragments of backsheet may firmly stick to the undergarment and may be very difficult to remove in the absence of a graspable portion which can be used to peel off the fragment.

There is therefore a need to identify an improved backsheet/fastening adhesive combination which is strong enough to keep the article in place during its usage and which at the same time allow the use of thinner backsheets without causing their rupture when the article is removed from the undergarment.

SUMMARY OF THE INVENTION

Figure 1:
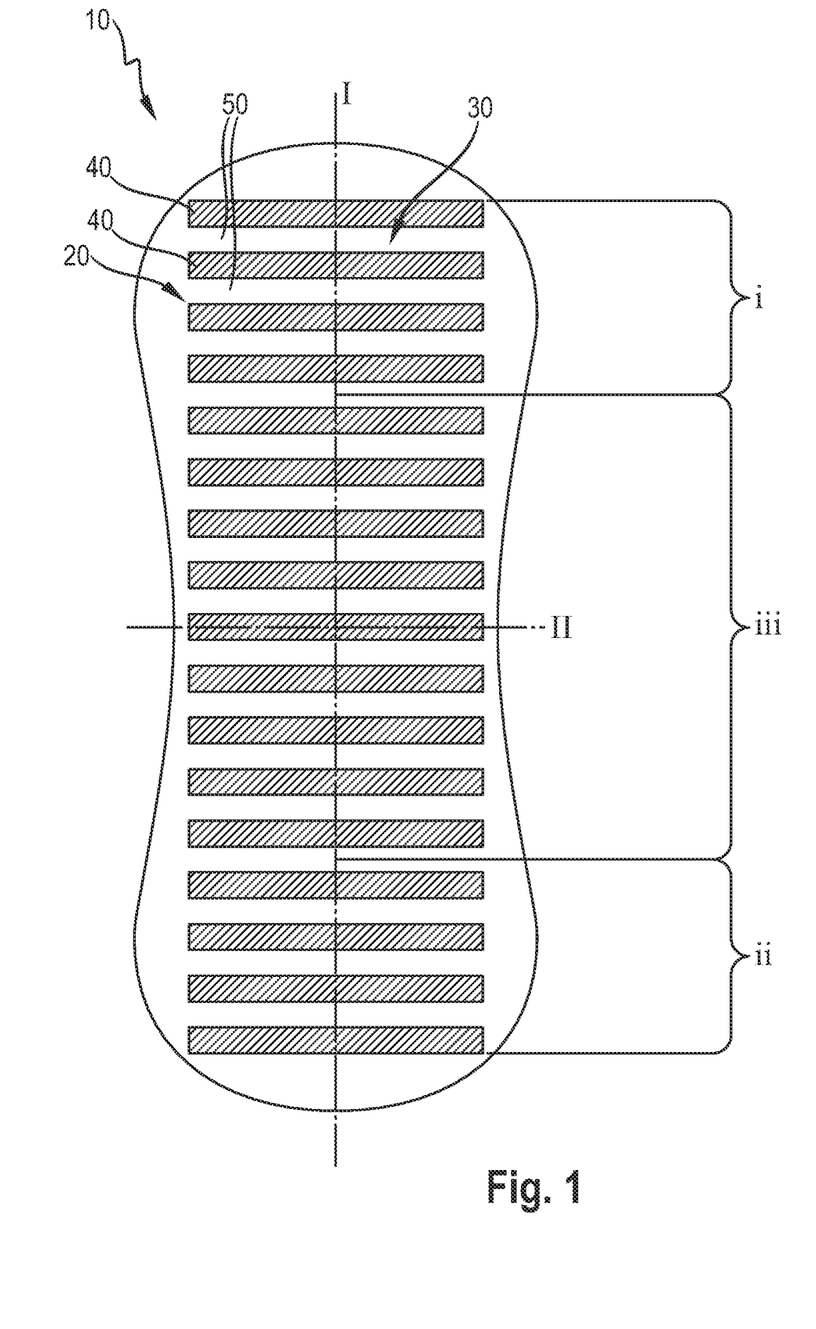
FIG. 1 represents an absorbent article according to the invention.
Figure 2:
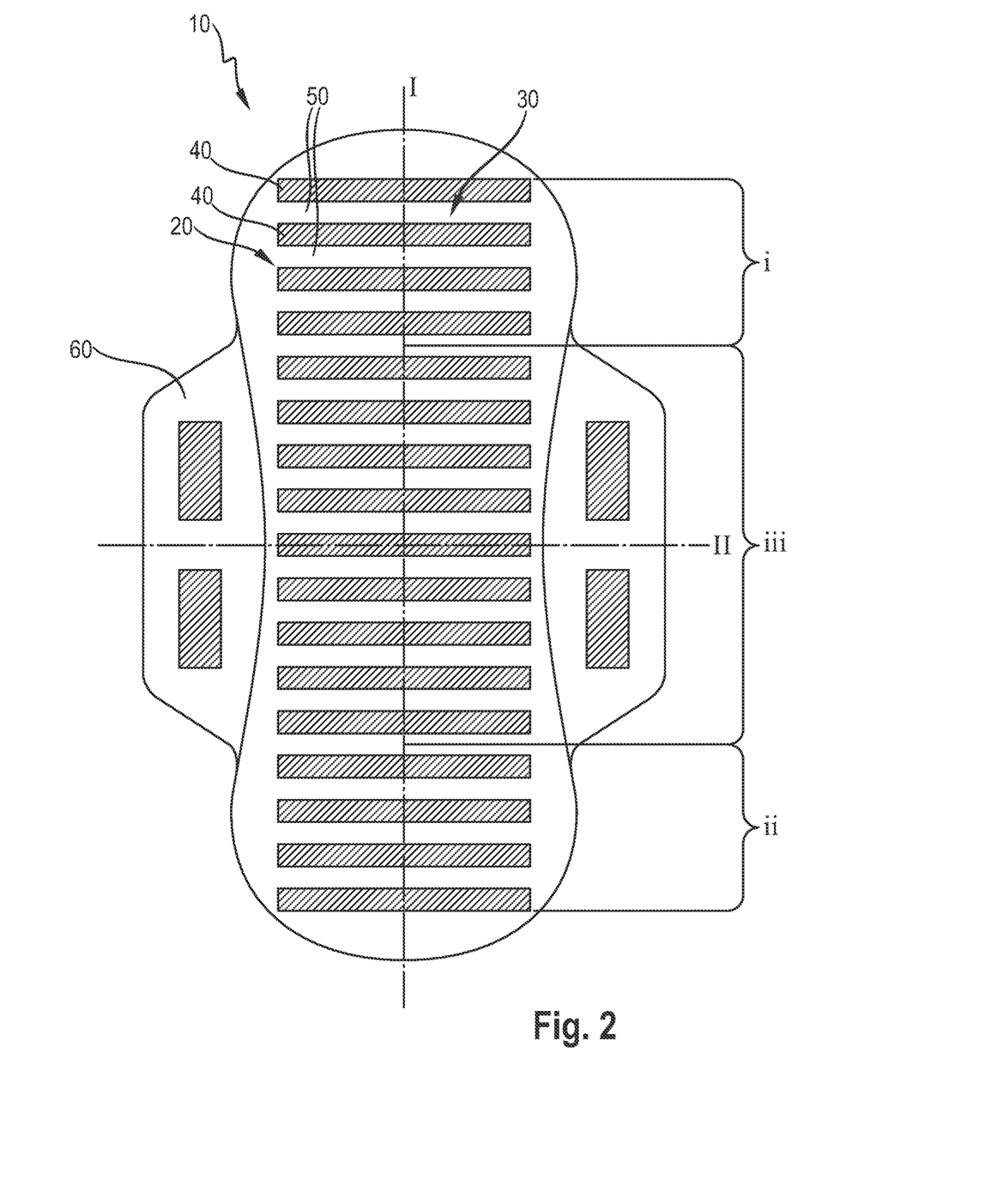
FIG. 2 represents an absorbent article with wings according to the invention.

The present invention relates to an absorbent article (10) selected from a sanitary napkin, an incontinence pad and a pantyliner, having a body-facing surface and a garment-facing surface, The absorbent article also has a longitudinal axis (I), a transversal axis (II), a front end portion (i), a rear end portion (ii) and a central portion (iii). The absorbent article comprises:
  a topsheet layer;
  a backsheet layer (20);
  optionally one or more intermediate layers enclosed between topsheet and backsheet (20)
  a fastening adhesive (PFA) applied on the backsheet garment facing surface.
At least a portion of the fastening adhesive (PFA) is applied in a pattern (30) and the backsheet layer (20) is a plastic film having a basis weight of less than 22 gsm or less than 20 gsm or less than 18 gsm or less than 15 gsm.

The absorbent articles of the present invention use less plastic and are softer than comparable articles, and at the same time do not present negatives in terms of backsheet tearing upon peeling from underwear and stay in place performance during use.

DETAILED DESCRIPTION OF THE INVENTION

"Absorbent articles" refers to devices that absorb and contain body exudates, such as urine, menses, and feces. The term "disposable" is used herein to describe absorbent articles which are not intended to be laundered or otherwise restored or reused as an absorbent article after a single use. Examples of absorbent articles include diapers, toddler training pants, adult incontinence garments, and feminine hygiene garments such as sanitary napkins, pantiliners, interlabial devices, hemorrhoid pads, and the like. Absorbent articles according to the present invention are selected from sanitary napkins, incontinence pads and pantyliners.

Absorbent articles and components thereof according to the present invention, including the topsheet, backsheet, absorbent core, and any individual layers of these components, have a body-facing surface and a garment-facing surface. As used herein, "body-facing surface" means that surface of the article or component which is intended to be worn toward or adjacent to the body of the wearer, while the "garment-facing surface" is on the opposite side and is intended to be worn toward or placed adjacent to the wearer's undergarments when the disposable absorbent article is worn.

In general, the absorbent articles of the present invention comprise a topsheet, a backsheet, and (with the exception of thin pantyliners which are not meant to absorb fluids but just to provide a clean feeling to the panties) an absorbent core disposed between the topsheet and backsheet and eventually other optional intermediate layers.

The term "longitudinal", as used herein, refers to a line, axis, or direction in the plane of the absorbent article that is generally aligned with (i.e., approximately parallel to) a vertical plane that bisects a standing wearer into left and right body halves when the absorbent article is worn.

The term "transverse", as used herein, refers to a line, axis, or direction that generally lies within the plane of the article that is generally perpendicular to the longitudinal direction.

The topsheet of the absorbent article is preferably compliant, soft feeling, and non-irritating to the wearers skin and hair. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like.

The backsheet and the topsheet may sandwich one or more intermediate layers. These intermediate layers can comprise additional components of the absorbent articles such as typically, an absorbent core and one or more layers having acquisition and/or distribution properties which are typically disposed between absorbent core and topsheet (in which case are sometimes called "secondary topsheets" or between absorbent core and backsheet.

The secondary topsheet or acquisition layer can comprise a tissue layer or a nonwoven, such as carded resin-bonded nonwovens, embossed carded resin-bonded nonwovens, high-loft carded resin-bonded nonwovens, carded through-air-bonded nonwovens, carded thermo-bonded nonwovens, spunbonded nonwovens, and the like. A variety of fibers can be used in the secondary topsheet or acquisition layer, including natural fibers, e.g. wood pulp, cotton, wool, and the like, as well as biodegradable fibers, such as polylactic acid fibers, and synthetic fibers such as polyolefins (e.g., polyethylene and polypropylene), polyesters, polyamides, synthetic cellulosics (e.g., RAYON®, Lyocell), cellulose acetate, bicomponent fibers, and blends thereof. The basis weight of the secondary topsheet or acquisition layer can vary depending upon the desired application.

The absorbent core can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers. Other suitable absorbent core materials include absorbent foams such as polyurethane foams or high internal phase emulsion ("HIPE") foams. Suitable HIPE foams are disclosed in U.S. Pat. Nos. 5,550,167, 5,387,207, 5,352,711, and 5,331,015.

For some absorbent articles, the absorbent core can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa.

The absorbent core can comprise superabsorbent materials such as absorbent gelling materials (AGM), including AGM fibers, as is known in the art. The absorbent core can therefore constitute a layer comprising superabsorbent material.

According to an embodiment of the present invention, the superabsorbent material for the absorbent core can be selected among polyacrylate based materials, typically in particle form, as described in U.S. Patent Application No. 2008/0172017 A1. The polyacrylate based materials incorporated in the absorbent articles of the present invention are polyelectrolytes with a multiplicity of anionic functional groups, typically carboxyl groups. In certain embodiments, the polyacrylate based materials can comprise polyacrylates, polymethacrylates, and derivatives thereof, such as for example polyacrylate sodium, polymethacrylate sodium, polyacrylate potassium, polymethacrylate potassium, starch grafted polyacrylate, starch grafted polymethacrylate, polyvinyl alcohol grafted polyacrylate, polyvinyl alcohol grafted polymethacrylate, cellulose grafted polyacrylate, cellulose grafted polymethacrylate, and the like. In an embodiment of the present invention, the absorbent gelling material can be a crosslinked, partially neutralized polyacrylate.

The polyelectrolytes which provide the polyacrylate based materials incorporated in the absorbent articles of the present invention can be made from polymerizable, unsaturated, acid-containing monomers. Such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids, and mixtures thereof.

Polyacrylate based materials, typically partially neutralized polymers, are commonly incorporated in absorbent articles and are known as superabsorbent polymers or superabsorbents, and are crosslinked. The polyacrylate material has neutralized, typically with sodium, carboxylate groups hanging off the main polymer chain. In contact with water, the sodium detaches and goes in solution, leaving only carboxyl ions. Being negatively charged, these ions repel one another so that the polymer unwinds and absorbs more and more water, which is instead attracted by the carboxyl ions, as further carboxyl ions become available. The hydrogen in water is trapped by the polyacrylate due to the atomic bonds associated with the polarity forces between the atoms. The cross-links, which bridge different polymer chains, lead to a three dimensional structure, which upon liquid absorption constitutes the swollen gel.

According to an embodiment of the present invention, the absorbent gelling material which can be comprised in the absorbent core can be selected among the polyacrylate based polymers described in the European Patent Application EP 05023061.4, filed on 21 Oct. 2005 in the name of The Procter and Gamble Company. As explained in the referenced application, polyacrylate based materials being very slightly crosslinked, or substantially not crosslinked at all, incorporated in absorbent articles for the absorption of proteinaceous or serous body fluids such as for example menses, blood, plasma, vaginal secretions, and also mucus or milk, but particularly menses or blood, provide an improved absorption and retention capacity for such body fluids, and an improved absorption rate as well, compared to traditional crosslinked superabsorbents.

According to the above referenced application, a measure of the degree of crosslinking of a polyacrylate based polymer can be expressed in terms of the soluble or extractable fraction of the polymer. As it is known in the art, lower molecular weight polymer chains can be solubilized, or extracted, from the polymer in certain conditions, and represent said soluble or extractable fraction of the polymer itself. Generally, the extractable fraction can be considered to be inversely proportional to the degree of crosslinking, that is, the higher the degree of crosslinking, the lower the fraction, since a greater proportion of the polymer mass is actually incorporated into the polymer network. Such polyacrylate based polymer which can be incorporated in an absorbent article for absorption of proteinaceous or serous body fluids, particularly menses, has an extractable fraction of at least about 30% by weight, between about 30% and about 80% by weight, or between about 32% and about 70% by weight, evaluated according to the Extractables test method described in the PCT Patent Application WO 07/047598. Alternatively, said polyacrylate based materials can have a retention capacity of at least about 30 g/g, at least about 35 g/g, or at least about 40 g/g, evaluated according to the Centrifuge Retention Capacity test described in the PCT Patent Application WO 07/047598.

The absorbent gelling materials can be typically used in the form of discrete particles. Such absorbent gelling materials can be of any desired shape, e.g., spherical or semi-spherical, cubic, rod-like polyhedral, etc. Shapes having a large greatest dimension/smallest dimension ratio, like needles and flakes, are also contemplated for use herein. Agglomerates of absorbent gelling material particles may also be used.

Absorbent cores may include a core wrap i.e. a thin layer of fluid pervious material (usually a tissue paper or a think nonwoven layer) which wraps the core in order to preserve its integrity during manufacturing of the article and during its use.

The absorbent article can comprise further components such as side cuffs, typically found in incontinence pads, or side wings or side flaps, typically found in sanitary napkins.

The absorbent articles herein are preferably disposable after a single use and are usually commercialized in packages comprising multiple units which in some cases can be individually wrapped.

The backsheet of the absorbent articles of the present invention is the outer layer of the article on the garment facing side. A fastening adhesive (also called PFA: Panty fastening Adhesive) is applied on the garment facing surface of the backsheet. In case the outer layer of the absorbent article on its garment facing side is a composite material (such as a laminate of a film and a nonwoven material) for the purpose of the present invention the term "backsheet" indicates exclusively the outermost layer of the layers forming said composite material. For example in the case of a NW/PE film laminate with the PE film being the outer layer on which garment facing surface the fastening adhesive is applied, for the purpose of the present invention the term "backsheet" indicates exclusively said outer PE film layer. For the purpose of the present invention side flaps/side wings (which are often formed by extensions of one or both of topsheet and backsheet) are not considered part of the backsheet.

The backsheet of the absorbent articles of the present invention is a plastic film and is preferably flexible and soft. As used herein, the term "flexible and soft" refers to materials which are compliant and will readily conform to the general shape and contours of the human body and will give the users a pleasant tactile feel on the skin. The backsheet prevents the exudates absorbed and contained in the absorbent core from wetting articles which contact the absorbent article such as bedsheets, pants, pajamas and undergarments. The backsheet can also be vapor permeable ("breathable"), while remaining fluid impermeable. In this case typically microporous plastic films are used which are water vapor permeable while remaining essentially impermeable to liquids.

According to the present invention the backsheet is a plastic film having a basis weight of less than 22 gsm or less than 20 gsm or less than 18 gsm or less than 15 gsm.

The minimum basis weight usable in the present invention will depend on the mechanical characteristics of each film, which are influenced, as known in the art by the type of polymer used and by the technology used to prepare the film. A skilled person will be generally able to obtain sufficiently strong films at sufficiently low basis weight using the common general knowledge available. Plastic films for use in the present invention may have a basis weight of from 1 to 22 gsm or from 4 to 20 gsm or from 4 to 18 gsm or from 6 to 18 gsm or from 6 to 15 gsm.

Any type of plastic film can be used as backsheets according to the present invention. Suitable films can be formed by a thermoplastic polymeric material and can be obtained by known film making processes. Plastic films can be selected from single layer or multilayer films which are obtainable for example through a single layer extrusion or a multilayer co-extrusion process. For example US20140248484 discloses a method for producing thin plastic films usable as backsheets in the present invention wherein an initial film web made of a thermoplastic polymer material containing a polyethylene matrix, and 1 to 70 parts by weight of polypropylene per 100 parts by weight of polyethylene matrix, is, after being heated, guided through a cooled roll gap whereby the initial film web is heated only until the polyethylene matrix material melts but below the melting temperature of the polypropylene.

The plastic films usable herein as backsheets can comprise a single polymer or a blend of different polymers. In addition to polymers, the plastic films of the present invention can comprise additives such as for example pigments, dyes, chemical additives such as light protectors, anti-oxidants, and inert materials such as titanium oxide, calcium carbonate, or also kaolin, diatomaceous earth, or mixtures thereof. The presence of an inert component, typically calcium carbonate, can increase the physical properties of the polymeric film, particularly heat resistance, which can be beneficial in the context of the present invention, where backsheet films are typically heat sealed along the perimeter to the topsheet of the absorbent article. Also inert materials are sometime included in plastic films which are mechanically stretched when cold so that the inert particles form a network of channels which allows the passage of water vapor while maintaining a good permeability. Such films are normally identified as "microporous films" are suitable as backsheets in the present invention and they can provide improved breathability in the absorbent articles (as known in the art). The plastic films usable herein as backsheets of the present invention are preferably thermoplastic polyolefin based film. The plastic film for of the present invention can be for example a polyethylene (PE) based film, a polypropylene based (PP) or a PE/PP blend based film.

When it is mentioned that a film is "based" on a polymer (e.g. PE) or on a mixture of polymers (e.g. PE/PP blend), it is intended that the majority of the mass of the film is constituted by the polymer(s) of which is based on, preferably more than 80% wt. even more preferably more than 90% wt. The remaining mass of the film can be formed by other polymers and customary film additives as known in the art.

It has been found that films based on such polyethylene/polypropylene blends provide the required tensile strength at a surprisingly low basis weight and thickness, and hence these are particularly suitable as backsheets for the absorbent articles of the present invention. In case of a PE/PP blend based film, the film comprises more than 5%, or more than 10%, or more than 15%, or more than 25%, or more than 35% by weight of polypropylene.

A general principle known in the art is that, considering films film having a given composition and being prepared using a given process, thicker films will have higher tensile strength than those with a lower thickness. However low thickness films are preferred as they are softer and reduce the environmental impact of the articles and a balance has to be found between using films having the lowest possible thickness but still being able to withstand the stretches they are subject to during use and especially during detachment from the underwear after use.

Plastic films particularly suitable as backsheets according to the present invention can be provided in order to have the selected characteristics in terms of low thickness and basis weight combined with desired mechanical properties, such as softness and tensile strength or tear propagation resistance, as explained above, by suitably acting on composition and/or process parameters as known to the skilled person. Parameters which can be varied to tune the mechanical properties of the films are for example polymer average molecular weight, density, molecular branching degree, film material composition as explained above with reference to possible polypropylene content, or film layer structure. Alternatively or in combination process conditions may be selected, for example type of extrusion, e.g. cast or blown extrusion, cooling, stretching, embossing in order to obtain the final plastic film for the backsheet according to the present invention. A person skilled in the art of film making is generally capable to manipulate these variables in order to obtain a film with the desired properties.

The plastic film of the present invention may have a maximum tensile strength of at least 2.9 N/cm, or of at least 5.0 N/cm, or of at least 6.0 N/cm, or also of at least 7.0 N/cm. The tensile strength is measured according to the general ASTM D 882 Standard Test Method for Tensile Properties of Thin Plastic Sheeting, slightly modified as explained in the "Test Method" section below.

As known, the tensile strength of plastic films, is often not uniform in all directions, these films are said "anisotropic". Anisotropic films typically have a higher tensile strength value in the direction corresponding to the direction along which the film has been originally extruded, and has a lower value in the direction generally orthogonal to this. The plastic film used for the backsheet of the present invention has hence a maximum tensile strength, and a minimum tensile strength, the "maximum tensile strength" is then measured along the direction in which the tensile strength is higher which is generally the direction along which the film was originally extruded.

In the case of anisotropic film the plastic film of the backsheet can also preferably have a minimum tensile strength of at least 1.5 N/cm, or of at least 2.5 N/cm, or also of at least 3.5 N/cm.

In the case of anisotropic films it is generally preferred that, when these are incorporated as backsheets into absorbent articles, the direction along which the maximum tensile strength is measured is essentially parallel to the longitudinal axis of the absorbent article.

Alternatively, plastic films having a substantially uniform tensile strength in all directions, also known as isotropic materials, can be used for the backsheet according to the present invention. In such a case the required maximum tensile strength corresponds to the generic, uniform tensile strength of the flexible sheet material.

The plastic film for use as a backsheet in the present invention can also be selected in order to have a tear propagation resistance of at least 0.07 N, or of at least 0.20 N, or of at least 0.25 N. Independently or in combination the tear propagation resistance of the plastic film according to the present invention can also be less than 5 N, or less than 3 N, or less than 2 N. The tear propagation resistance can be evaluated according to the standard test method ASTM D 1938-06, slightly modified as explained in the "Test Methods" section below.

PFA: as mentioned above, the backsheet forms the garment-facing surface of the absorbent article on which the fastening adhesive is placed. The fastening adhesive (PFA) can comprise any adhesive or glue used in the art for such purposes. These adhesives typically are pressure sensitive and remain tacky well below their application temperature. For example PFA can be pressure sensitive hot melt adhesives.

Prior to use of the absorbent article, the areas being coated with PFA are typically protected from contamination and from adhering to another surface where this is not desired, by a protective cover means such as a silicone coated release paper, a silicone coated plastic film or any other easily removable cover. The protective cover means can be provided as a single piece or in a multitude of pieces, e.g. to cover individual adhesive areas (e.g. on the backsheet and on the wings). The protective cover means can also perform other functions such as provide individualized packaging for the article or provide a disposal function as known in the art. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

The PFA may be applied onto the garment-facing surface of the absorbent article, typically the backsheet and/or the wings, using any one of methods well known in the art for this purpose such as slot coating, spraying and roll printing. One method of applying the PFA to the garment-facing surface of the absorbent article is the direct coating on the backsheet; another method is printing the PFA onto a release paper, which is then pressed onto the garment-facing surface of the absorbent article. Thereby the PFA is transferred from the release paper to the garment-facing surface of the absorbent article. Such a procedure is described in EP 788,338.

The PFA is applied on the backsheet in order to ensure proper stay in place of the absorbent article during use. During use, the absorbent articles attached to the undergarment using the PFA are subject to various types of stress in different directions, so the strength of adhesion of the PFA must be very high in order to avoid any shift of the article. However, when an absorbent article is peeled off from an undergarment after its use, this is typically done by grasping one side of the article and exerting a force toward the opposite side. The force required to separate the PFA from the undergarment is applied, at any instant, on a narrow region of the backsheet, on the line of separation, film thus subjecting that specific region to an elevated stretch which can cause ruptures in some cases.

Rupture of the backsheet can have quite detrimental effects for the user of an absorbent article because a backsheet rupture can expose the absorbent core of the article, so that the user and its garments can be exposed to the body fluids which are retained within the article which can cause stains and hygienic problems. Moreover when backsheet rupture occurs, fragments of broken backsheet might remain stuck to the undergarment and be very difficult to remove due to the very strong adhesive and the lack of a grip portion. Often the removal of backsheet pieces requires strong abrasion or solvents which may damage expensive underwear. Therefore absorbent article manufacturers put a lot of efforts and attention in avoiding backsheet ruptures typically using relatively thick films as backsheets so that they can resists stronger stretching forces without tearing.

On the other hand there is a pressure to manufacture softer backsheets and to reduce plastic usage and consequent environmental impact of absorbent articles, so that thinner and lighter plastic film are desirable for this purpose but in general, at a parity of other characteristics, a thinner films will have an reduced tensile strength and consequently an increased likelihood to break when detached from the undergarment.

In the present invention it was surprisingly found that by combining a patterned application of the PFA with a film having low thickness an absorbent article can be obtained which at the same time has the desired stay in place characteristics, does not have backsheet tearing problems, is softer and uses less plastic by using a thinner and lighter backsheet film.

In the present invention PFA is applied on the backsheet of the absorbent article and at least a portion of the PFA is applied in a pattern. For PFA applied in a pattern it is intended a discontinuous application of the PFA on the backsheet such that any portion of said application is never more than 10 mm distant from another portion of the backsheet where PFA is not applied. The PFA pattern can be a repeating or a non repeating pattern and can be formed by a plurality of separate or only partially connected elements which can be selected from any possible application pattern such as for example stripes, circles, dots, geometric figures, stars, decorative figures, irregular shapes, and the like.

When the user removes the article from the underwear typically grabs the article from one side edge and pulls it toward the opposite side. It has been surprisingly found that the stretch caused by the PFA on the backsheet upon article removal is not constant all along the removal operation but instead tends to increase with time, and the increase is steeper if the user pulls the article at a faster speed. It is believed this is due to the fact that, in addition to the initial stretch required to separate backsheet and glue, the backsheet also deforms elastically upon stretching so that an additional stretch caused by the elastic deformation adds to the stretch required to separate the PFA from the underwear. In case of uniform PFA application the elastic deformation progressively increases during the removal of the absorbent article and so it increases also the additional stretch exerted by it. When during removal of the article the sum of the stretches needed to separate PFA and underwear and the additional stretch due to the elastic deformation are above the tensile strength of the film, the film deforms plastically and then breaks. Breakages are typically localized because the PFA stretch is roughly proportional to the PFA basis weight and the distribution of PFA is typically not perfectly uniform so a backsheet tearing typically starts in correspondence with a point of higher PFA basis weight.

It has been surprisingly found that if the PFA is applied in a pattern instead of a continuous application backsheet tearing is avoided. It is believed that this is due to the fact that, when separating the absorbent article from the underwear, during the "peeling" process there is a sequence of areas with and without PFA: in correspondence of each area with no PFA applied, the elastic deformation of the backsheet film is "released" so to speak, and reset to an essentially zero stretch, so that, in the presence of a pattern, the component of stretch due to the elastic deformation of the backsheet is continuously reset to zero at any element of the pattern instead of increasing all along during article removal. The PFA application pattern can be, for example a striped pattern formed by a succession of parallel stripes alternating PFA stripes and PFA free stripes. A striped PFA application pattern can be applied in any direction. A preferred orientation of the stripes is a direction perpendicular to the direction along which the article is pulled during removal from the undergarment. Absorbent article users remove absorbent articles from the undergarments pulling them along either their longitudinal or transverse axis so a PFA pattern where the stripes are parallel to each other and oriented in transversal or longitudinal direction (respectively) can be used. Instructions can be provided with the absorbent article to follow a preferential direction of removal in order to fully enjoy the benefits of the invention. As most absorbent article users remove absorbent articles from the undergarments pulling them along their longitudinal axis, a PFA pattern where the stripes are parallel to each other and oriented in transversal direction is preferred.

A PFA pattern of stripes in transversal direction has the additional advantage to allow an excellent stay in place performance with a lower amount of glue. It is believed this is due to the fact that most of the pressures and stretches which are exerted on an absorbent article during use are caused by the leg movements. Leg movements essentially cause compression along the transversal axis and in alternate opposite directions, so that, in case of detachment the absorbent article tends to move sideways along the transversal axis. With a striped PFA pattern having stripes oriented along the transverse direction the article offers a higher resistance to shifting along that direction because the PFA has a continuous application along that direction. On the contrary when the PFA is applied in stripes along the longitudinal direction the article will offer higher resistance to shifting along the longitudinal direction.

In all striped patterns the PFA stripes can have any length, they can for example extend from one edge of the article to the opposing edge or the can be shorter so to leave an unattached portion at the edge of the article which might be used as gripping portion when removing the absorbent article.

In a striped pattern the PFA stripes can have any thickness, for example they can have a width from 1-10 mm, or a width from 1 to 6 mm. The PFA free stripes can have a width from 1 to 10 mm or from 1 to 6 mm. In some cases it is preferred that, in a striped pattern, on average the PFA free stripes have a lower width than the PFA stripes, so that, as a result, more than 50% or more than 60% of the total surface of the area where the PFA pattern is present is covered by PFA.

In a striped pattern all the PFA stripes can have the same width throughout the pattern or each PFA stripe can have different width throughout the pattern.

Similarly, in a striped pattern all the PFA free stripes can have the same width throughout the pattern or each PFA free stripe can have different width throughout the pattern.

In the case the PFA stripes have a different width throughout the pattern, the PFA stripes may have a larger width at least one end portion (or at both end portions) of the absorbent article and a smaller width at a central portion of the absorbent article.

As mentioned above the PFA is applied on at least a portion of the backsheet of the absorbent article in a pattern. In some cases the PFA is applied on the entire backsheet in a pattern.

In other cases the PFA is applied in a pattern over one or more portions of the backsheet and as a continuous application on the remaining portion(s) of the backsheet. Also, in all cases, some portions of the backsheet, outside the portion(s) with the patterned application, can be free of PFA.

FIG. 1 represents an exemplary absorbent article (10) according to the invention seen from the garment facing side. The article of FIG. 1 has a longitudinal axis (I) a transversal axis (II), a front end portion (i) a rear end portion (ii) and a central portion (iii) and is a sanitary napkin (10) without wings and its backsheet (20) comprises a pattern (30) of PFA in the form of a succession of PFA stripes (40) and PFA free stripes (50).

Optional wings (also called "side panels") are common elements in absorbent articles according to the present invention as known to the persons skilled in the art. The intent of the wings is to protect the sides of the undergarments and typically wings fold along the crotch area of the underwear and are attached below it.

Wings can be provided as separate pieces and be attached to the article, typically a pantyliner or a sanitary napkin, or they can be integral with the materials of the absorbent articles, e.g., by being an integral extension of the topsheet, the backsheet, or of both.

As mentioned above, for the purpose of the present invention, wings are not considered part of the backsheet (even when they are formed by an integral extension of it). Wings typically include PFA on the backsheet side in order to affix them below the crotch of the underwear, and any typical PFA distribution can be used in the present invention, such as a continuous application or a patterned application, for example a patterned application of PFA on the wings may provide the same benefits as the patterned PFA application on the backsheet of the article when the article is removed thus reducing the risk of tearing the wing material. For example at least a portion of the wing back surface can comprise a patterned application of PFA in the same forms described above for the patterned PFA application on the backsheet e.g. a discontinuous application of the PFA such that any point of said application is never more than 10 mm distant from another portion where PFA is not applied. The PFA pattern can be formed by a plurality of separate or only partially connected elements which can be selected from any possible application pattern such as for example stripes, circles, dots, geometric figures, stars, decorative figures, irregular shapes, and the like. For example stripes or squares of PFA are particularly suitable patterns.

FIG. 2 represents an exemplary absorbent article according to the invention seen from the garment facing side. The article of FIG. 2 has a longitudinal axis (I) a transversal axis (II), a front end portion (i) a rear end portion (ii) and a central portion (iii) and is a sanitary napkin (10) with wings (60) and its backsheet (20) comprises a pattern (30) of PFA in the form of a succession of PFA stripes (40) and PFA free stripes (50). The article also comprises a PFA pattern on its wings (70) in the form of four squares.

Test Methods.
Tensile strength.
The tensile strength of the plastic film of the present invention is evaluated according to the standard test method ASTM D 882-02 modified as specified below, and is the tensile strength corresponding to the maximum load. The following sections, unless otherwise indicated, replace the respective corresponding sections in the original ASTM D 882-02 test method.

Section 6.1— The test specimens shall consist of strips of uniform width and thickness at least 20 mm longer than the grip separation used, or even slightly less, provided slippage relative to the grips is prevented as prescribed in Section 5.1.3.3.

Section 6.2— The nominal width of the specimens shall be 25.4 mm

Sections 9.2 and 9.3— The speed of testing shall be set at 508 mm/min, which is optimized for plastic films typically suitable for constituting the backsheet according to the present invention. The initial strain rate is therefore not considered.

Section 10.2— Measurement of the cross-sectional area of the specimen as a function of its width and thickness, as provided by original Section 10.2 of ASTM D 882-02, does not apply, as the tensile strength value is expressed as force per unit length, see Section 11.3 below.

Section 10.3— Set the initial grip separation at 51 mm

Section 10.4— Set the rate of grip separation at 508 mm/min, see Section 9.2 above. Set a pre-load value at 0.075 N. Pre-load is meant to compensate for slack that may be present in the specimen when loaded by finding the first point at which the measured load (force) exceeds the input pre-load, and assigning an elongation value of zero at this point. Zero the calibrated load weighing, the extension indicator with the proviso above due to the set pre-load value, and the recording system.

Section 10.6— In addition to the provisions of original Section 10.6, care shall be taken when placing the specimen to not exceed the selected pre-load value of 0.075 N. The instrument shall not be zeroed after the specimen has been placed.

Section 11.3— Tensile Strength (nominal) shall be calculated by dividing the maximum load by the original width of the specimen (25.4 mm). The result shall be expressed in force per unit length, usually Newton per centimeter. This value shall be reported to two significant figures.

In general, the selected rate of grip separation and the initial distance between the grips are optimized for plastic films suitable for constituting the backsheet according to the present invention. In principle, the provisions of original Sections 9.2, 9.3, 10.3, 10.4 of ASTM D 882-02 shall apply. As also explained in the description above, the plastic film of the present invention can be anisotropic, i.e. have different tensile strengths in different directions of stress. In this case, the provision of Section 6.6 of ASTM D 882-02 shall apply. For measurements of the wrapper material of an actual product, as already explained, different test specimens shall be actually prepared having their long axes respectively parallel to the major and to the minor axis of the backsheet material laid open flat on a plane surface, usually to the longer and shorter sizes thereof.

When the tensile strength of a backsheet of an actual product has to be measured, the backsheet of the article can be treated with dichloromethane to remove the fastening adhesive, then a portion of the backsheet can be cut out and can be separated from other internal layers to which it might be glued using dichloromethane.

Tear-Propagation Resistance.
The tear propagation resistance of the plastic film of the present invention is evaluated according to the standard test method ASTM D 1938-06, with some modifications as explained below.

The die shape, referred to in Section 6.3 and FIG. 3 of the ASTM method, is changed such that its length is reduced to 40 mm while its width remains 25 mm. The length of the precut forming tongues A and B is reduced to 15 mm, the unslit portions remains 25 mm as in FIG. 3 of the ASTM method. The two tongues A and B are now 15 mm long. In order to make them 50 mm long as in FIG. 3 of the ASTM method 2 strips of adhesive tape Tesa 7475 are cut in size 12.5 mm×45 mm and are attached on the front and on the back of the tongue A superimposing to it for 10 mm and essentially making the tongue longer. As a result the tongue is long 50 mm Other 2 equal strips of adhesive tape are attached in the same way to tongue B so that at the end the specimen to be tested will have exactly the same size, size of the tongues and size of the precut of the specimen in FIG. 3 of the ASTM method.

The grip separation speed, referred to in Section 9.2, is 300 mm/min; with reference to subsequent Section 9.3, the test is continued until the tear has propagated through the entire unslit portion.

As for Section 10.1, the average tear propagation force is calculated by averaging the load over a 25 mm interval.

The tear propagation resistance is considered to correspond to the average tear propagation force for plastic films having a load-time chart as that of FIG. 1 in the ASTM method, called "low-extensible films" therein. The tear propagation resistance is instead meant to correspond to the initial tear propagation force for plastic films having a load-time chart as that of FIG. 2 in the ASTM method, called "highly extensible films" therein. Plastic films according to the present invention can more likely have load-time charts characterized by FIG. 1.

In the context of the present invention the tear propagation resistance is intended with reference to a tear along a direction orthogonal to the longitudinal axis of the absorbent article. Specimens have to be cut from the raw material or from the absorbent articles in order to match this orientation. When the tear propagation resistance of a backsheet of an actual product has to be measured, the backsheet of the article can be treated with dichloromethane to remove the fastening adhesive, then a portion of the backsheet can be cut out and can be separated from other internal layers to which it might be glued using dichloromethane.

In all cases where a percentage is mentioned within the present application it is intended to be a percentage by weight, unless specified otherwise.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

What is claimed is:

1. An absorbent article, comprising:
a longitudinal axis;
a transversal axis;
a topsheet layer;
a backsheet layer;
optionally one or more intermediate layers enclosed between said topsheet and said backsheet; and
an undergarment fastening adhesive applied in a pattern on an exterior surface of said backsheet, said pattern extending from a front end portion through a central portion and a rear end portion of said absorbent article;
wherein said backsheet comprises a plastic film having a basis weight of less than 22 grams per square meter and wherein said plastic film is an outermost layer of said absorbent article;
wherein said pattern comprises a plurality of separate spaced apart geometric figures comprising a length and a width, some of said plurality of separate spaced apart geometric figures being disposed in said front end portion, others of said plurality of separate spaced apart geometric figures disposed in said rear end portion, and the remainder of said plurality of separate spaced apart geometric figures disposed in said central portion, and said pattern further comprising at least one undergarment fastening adhesive free area disposed between each of said separate spaced apart geometric figures; and
wherein said length is oriented substantially perpendicular to said longitudinal axis of said absorbent article; and
wherein said adhesive is applied in said pattern on substantially an entirety of said backsheet so that more than 50% of said total surface of the area where said pattern is present is covered by said adhesive.

2. An absorbent article according to claim 1 wherein said plastic film is a thermoplastic polyolefin based film.

3. An absorbent article according to claim 2 wherein the plastic film is selected from polyethylene, polypropylene and polyethylene/polypropylene based films.

4. An absorbent article according to claim 2 wherein the plastic film is selected from polyethylene/polypropylene based films comprising more than 5%, by weight of the plastic film, of polypropylene.

5. An absorbent article according to claim 1 wherein said geometric figures comprises rectangular stripes.

6. An absorbent article according to claim 1 wherein said plastic film has a maximum tensile strength of at least 2.9 Newtons per square centimeter.

7. An absorbent article according to claim 1 wherein said plastic film has a tear propagation resistance of at least 0.07 Newtons.

8. An absorbent article according to claim 1 wherein the plastic film has a basis weight of less than 20 grams per square meter.

9. An absorbent article, comprising:
a longitudinal axis;
a transversal axis;
a topsheet layer;
a backsheet layer;
optionally one or more intermediate layers enclosed between said topsheet and said backsheet; and
an undergarment fastening adhesive applied in a pattern on an exterior surface of said backsheet, said pattern extending from a front end portion through a central portion to a rear end portion of said absorbent article;
wherein said adhesive is applied in said pattern on substantially an entirety of said backsheet so that more than 50% of the total surface of the area where said pattern is present is covered by said adhesive, wherein said pattern comprises a plurality of separate spaced apart stripes, each comprising a length and a width, and at least one undergarment fastening adhesive free area disposed between each of the separate spaced apart stripes, wherein some of said plurality of separate spaced apart stripes are disposed in said front end portion, wherein some of said plurality of separate spaced apart stripes are disposed in said rear end portion, and wherein some of said plurality of separate spaced apart stripes are disposed in said central portion;

wherein said backsheet comprises a plastic film having a basis weight of less than 22 grams per square meter; and wherein said length is oriented substantially perpendicular to said longitudinal axis of said absorbent article;

wherein said plastic film is an outermost layer of said absorbent article; and wherein said plastic film has a maximum tensile strength of at least 2.9 Newtons per square centimeter.

10. An absorbent article according to claim 9 wherein said plastic film has a basis weight of from 6 to 15 grams per square meter.

11. An absorbent article according to claim 9 wherein said plastic film has a maximum tensile strength of at least 5.0 Newtons per square centimeter.

12. An absorbent article according to claim 9 wherein said plastic film has a maximum tensile strength of at least 6.0 Newtons per square centimeter.

13. An absorbent article according to claim 9 wherein said plastic film has a maximum tensile strength of at least 7.0 Newtons per square centimeter.

14. An absorbent article, comprising:
a longitudinal axis;
a transversal axis;
a topsheet layer;
a backsheet layer;
optionally one or more intermediate layers enclosed between said topsheet and said backsheet; and
an undergarment fastening adhesive applied in a pattern on an exterior surface of said backsheet, said pattern extending from a front end portion through a central portion to a rear end portion of said absorbent article;

wherein said adhesive is applied in said pattern on substantially an entirety of said backsheet so that more than 50% of the total surface of the area where said pattern is present is covered by said adhesive, wherein said pattern comprises a plurality of separate spaced apart stripes, each comprising a length and a width, and at least one undergarment fastening adhesive free area disposed between each of said separate spaced apart stripes, wherein some of said plurality of separate spaced apart stripes are disposed in said front end portion, wherein some of said plurality of separate spaced apart stripes are disposed in said rear end portion, and wherein some of said plurality of separate spaced apart stripes are disposed in said central portion;

wherein said backsheet comprises a plastic film having a basis weight of less than 22 grams per square meter; and wherein said plastic film has a tear propagation resistance of at least 0.07 Newtons.

15. An absorbent article according to claim 14 wherein said plastic film has a tear propagation resistance of at least 0.20 Newtons but less than 5.0 Newtons.

16. An absorbent article according to claim 14 wherein said plastic film has a tear propagation resistance of at least 0.20 Newtons but less than 3.0 Newtons.

17. An absorbent article according to claim 14 wherein said plastic film has a tear propagation resistance of at least 0.20 Newtons but less than 2.0 Newtons.

18. An absorbent article according to claim 14 wherein said pattern comprises a plurality of spaced apart stripes, each having a major dimension oriented substantially parallel to said transversal axis of said absorbent article.

* * * * *